(12) United States Patent
Igarashi

(10) Patent No.: US 10,574,866 B2
(45) Date of Patent: Feb. 25, 2020

(54) IMAGING UNIT AND ENDOSCOPE APPARATUS

(71) Applicant: OLYMPUS CORPORATION, Tokyo (JP)

(72) Inventor: Takatoshi Igarashi, Ina (JP)

(73) Assignee: OLYMPUS CORPORATION, Tokyo (JP)

( * ) Notice: Subject to any disclaimer, the term of this patent is extended or adjusted under 35 U.S.C. 154(b) by 713 days.

(21) Appl. No.: 15/078,062

(22) Filed: Mar. 23, 2016

(65) Prior Publication Data

US 2016/0205296 A1    Jul. 14, 2016

Related U.S. Application Data

(63) Continuation of application No. PCT/JP2014/070250, filed on Jul. 31, 2014.

(30) Foreign Application Priority Data

Sep. 30, 2013   (JP) ................................. 2013-204949

(51) Int. Cl.
*H04N 5/225*    (2006.01)
*H04N 5/378*    (2011.01)
(Continued)

(52) U.S. Cl.
CPC ........... *H04N 5/2253* (2013.01); *A61B 1/005* (2013.01); *A61B 1/0008* (2013.01);
(Continued)

(58) Field of Classification Search
CPC . H04N 5/2253; A61B 1/0008; A61B 1/00114; A61B 1/005; A61B 1/051
(Continued)

(56) References Cited

U.S. PATENT DOCUMENTS 5,418,566 A    5/1995   Kameishi
2001/0007051 A1*  7/2001  Nakashima .............. A61B 1/05
600/179
(Continued)

FOREIGN PATENT DOCUMENTS

CN     101548535 A    9/2009
JP     H02277280 A   11/1990
(Continued)

OTHER PUBLICATIONS

Extended Supplementary European Search Report dated Feb. 16, 2017 in related European Patent Application No. 14 84 7039.6.
(Continued)

*Primary Examiner* — Sath V Perungavoor
*Assistant Examiner* — Kristin Dobbs
(74) *Attorney, Agent, or Firm* — Scully, Scott, Murphy & Presser, P.C.

(57) ABSTRACT

An imaging unit includes: an image sensor having an electrode pad and a light-receiving surface; a flexible printed circuit board having an inner lead connected to the electrode pad and extending from the image sensor in a direction opposite to where the light-receiving surface is provided; and one or more electronic components mounted on a first surface of the flexible printed circuit board, the first surface being on a side where the image sensor is provided. The flexible printed circuit board includes: an insulating base material; a first wiring layer on the base material on a side of the first surface; a first film for insulating the first wiring layer; a second wiring layer on the base material on a side of a second surface opposite to the first surface; and a second film for insulating the second wiring layer. The inner lead extends from the first wiring layer.

8 Claims, 14 Drawing Sheets

(51) Int. Cl.
*A61B 1/005* (2006.01)
*A61B 1/00* (2006.01)
*A61B 1/05* (2006.01)

(52) U.S. Cl.
CPC .......... *A61B 1/00114* (2013.01); *A61B 1/051* (2013.01); *H04N 5/2254* (2013.01); *H04N 5/378* (2013.01); *H04N 2005/2255* (2013.01)

(58) Field of Classification Search
USPC .......................................................... 348/76
See application file for complete search history.

(56) References Cited

U.S. PATENT DOCUMENTS

| | | | |
|---|---|---|---|
| 2001/0024848 A1* | 9/2001 | Nakamura | H01L 27/14609 438/200 |
| 2008/0023784 A1 | 1/2008 | Nakayama | |
| 2008/0111907 A1* | 5/2008 | Ito | H04N 5/2253 348/311 |
| 2009/0268019 A1 | 10/2009 | Ishii et al. | |
| 2010/0201794 A1* | 8/2010 | Kido | A61B 1/00124 348/65 |
| 2015/0358518 A1 | 12/2015 | Ishii et al. | |

FOREIGN PATENT DOCUMENTS

| | | |
|---|---|---|
| JP | H06113214 A | 4/1994 |
| JP | H09223722 A | 8/1997 |
| JP | 2000232957 A | 8/2000 |
| JP | 2001257937 A | 9/2001 |
| JP | 2003-010111 A | 1/2003 |
| JP | 2008034505 A | 2/2008 |
| JP | 2010005148 A | 1/2010 |
| JP | 2012050756 A | 3/2012 |
| WO | 2011092903 A1 | 8/2011 |

OTHER PUBLICATIONS

Japanese Office Action dated Mar. 13, 2018 in Japanese Patent Application No. 2013-204949.
International Search Report dated Nov. 4, 2014 issued in PCT/JP2014/070250.

* cited by examiner

IMAGING UNIT AND ENDOSCOPE APPARATUS

CROSS-REFERENCE TO RELATED APPLICATIONS

This application is a continuation of PCT international application Ser. No. PCT/JP2014/070250 filed on Jul. 31, 2014 which designates the United States, incorporated herein by reference, and which claims the benefit of priority from Japanese Patent Application No. 2013-204949, filed on Sep. 30, 2013, incorporated herein by reference.

BACKGROUND

1. Technical Field

The disclosure relates to an imaging unit and an endoscope apparatus, the imaging unit being provided at a distal end of an insertion unit of an endoscope that is configured to be inserted into a subject to image the inside of the subject.

2. Related Art

Endoscope apparatuses have been widely used to perform various examinations in a medical field and an industrial field. Among those apparatuses, a medical endoscope apparatus is widely used because an in-vivo image of a body cavity can be acquired without making an incision on a subject such as a patient by inserting an elongated, flexible insertion unit provided with an image sensor at a distal end thereof into the body cavity of the subject and, at the same time, a curative treatment can be performed as needed by projecting a treatment tool from the distal end of the insertion unit.

Fitted to the distal end of the insertion unit of such endoscope apparatus is an imaging unit including a solid state image sensor and a flexible printed circuit board (hereinafter referred to as an FPC board) employing Tape Automated Bonding (TAB) or the like and populated with electronic components such as a capacitor and an IC chip constituting a drive circuit of the solid state image sensor, where a signal cable is soldered to the FPC board of the imaging unit. An inner lead exposed from an end face of the FPC board is bent along a side of a light-receiving surface of the solid state image sensor from a side face thereof, and is connected to an electrode pad formed in the solid state image sensor.

As a technique of connecting the inner lead and the electrode pad, there is disclosed a technique in which an insulating carrier tape material of an FPC board is arranged on the side of a solid state image sensor, the FPC board being formed of the carrier tape material and a wiring layer including an inner lead formed from metal foil such as copper foil adhering to the carrier tape material (refer to Japanese Patent Application Publication No. 2001-257937, for example). Japanese Patent Application Publication No. 2001-257937 also discloses a technique in which the inner lead extending from a wiring pattern on the back side of a base material (back side of a surface on which an electronic component is mounted) of the FPC board is connected to the electrode pad of the solid state image sensor, the FPC board including the wiring pattern formed on both sides of the base material.

SUMMARY

In some embodiments, an imaging unit includes: a solid state image sensor having an electrode pad and a light-receiving surface and configured to receive light and to perform photoelectric conversion on the received light to generate an electrical signal; a flexible printed circuit board having an inner lead connected to the electrode pad of the solid state image sensor and extending from the solid state image sensor in a direction opposite to where the light-receiving surface of the solid state image sensor is provided; and one or more electronic components mounted on a first surface of the flexible printed circuit board, the first surface being on a side where the solid state image sensor is provided. The flexible printed circuit board includes: an insulating base material; a first surface-side wiring layer on the base material on a side of the first surface; a first surface-side electrical insulating film for insulating the first surface-side wiring layer; a second surface-side wiring layer on the base material on a side of a second surface opposite to the first surface; and a second surface-side electrical insulating film for insulating the second surface-side wiring layer. The inner lead extends from the first surface-side wiring layer.

In some embodiments, an endoscope apparatus includes an insertion unit, at a distal end of which the imaging unit is provided.

The above and other features, advantages and technical and industrial significance of this invention will be better understood by reading the following detailed description of presently preferred embodiments of the invention, when considered in connection with the accompanying drawings.

DETAILED DESCRIPTION

As modes for carrying out the invention (hereinafter referred to as "embodiment(s)"), an endoscope apparatus having an imaging unit will be described below. The present invention is not to be limited by the embodiments. The same reference signs are used to designate the same elements throughout the drawings. The drawings being provided schematically, one needs to further keep in mind that the relationship between the thickness and width of each member as well as a ratio of each member are different from actual ones. Moreover, the dimension and ratio of some parts are different among the drawings.

First Embodiment

Figure 1:
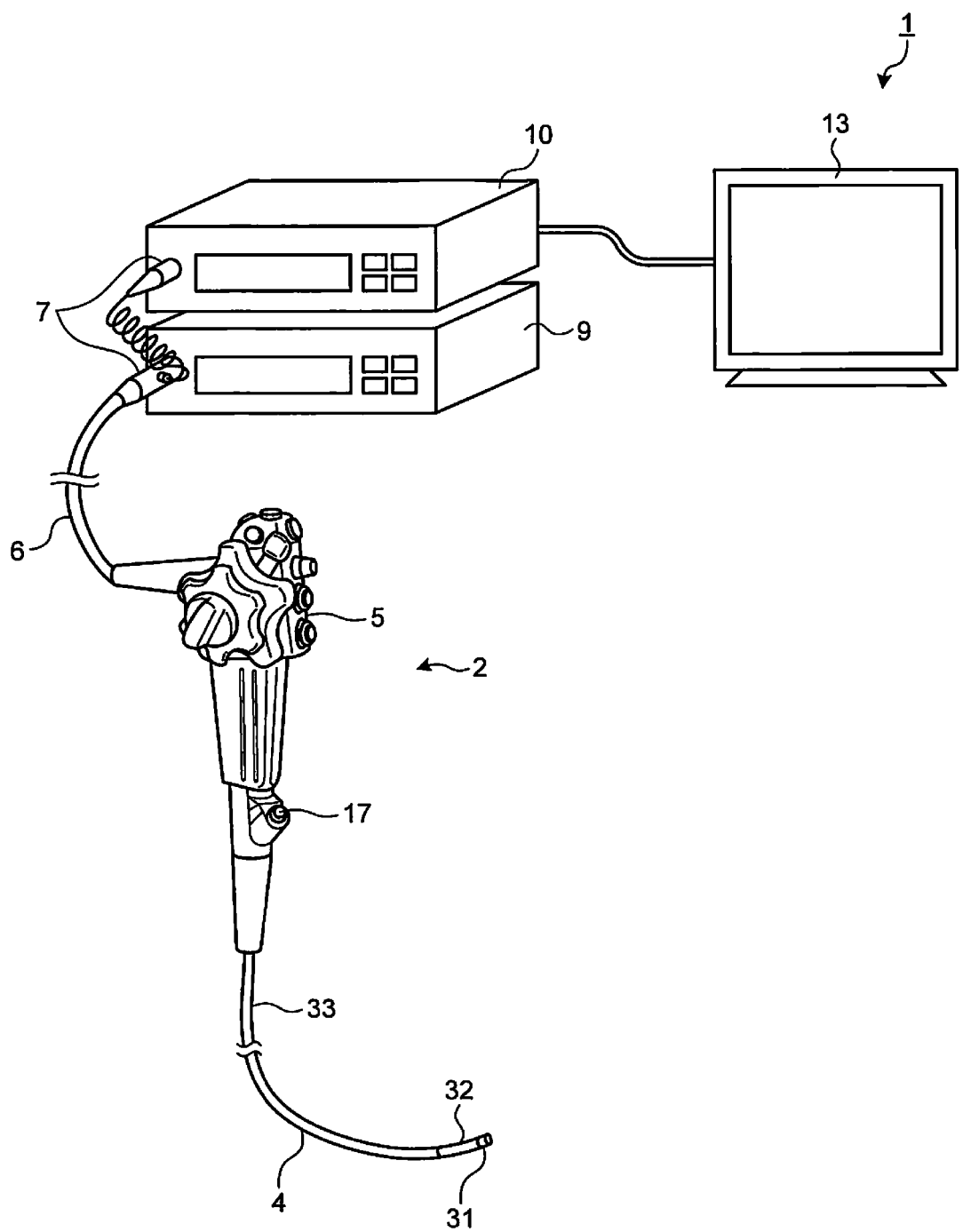
FIG. 1 is a diagram schematically illustrating an overall configuration of an endoscope system according to an embodiment of the present invention.

FIG. 1 is a diagram schematically illustrating an overall configuration of an endoscope system according to an embodiment of the present invention. As illustrated in FIG. 1, an endoscope apparatus 1 includes an endoscope 2, a universal cord 6, a connector 7, a light source device 9, a processor (control device) 10, and a display device 13.

The endoscope 2 images an in-vivo image of a subject by inserting an insertion unit 4 into a body cavity of the subject and outputs an imaging signal. An electric cable bundle inside the universal cord 6 extends to a distal end of the insertion unit 4 of the endoscope 2 and is connected to an imaging apparatus provided at a distal end portion 31 of the insertion unit 4.

The connector 7 is provided at a proximal end of the universal cord 6 and connected to the light source device 9 and the processor 10 to perform predetermined signal processing on an imaging signal output by the imaging apparatus at the distal end portion 31 connected to the universal cord 6, perform analog-digital conversion (A/D conversion) on the imaging signal, and output the signal as an image signal.

The light source device 9 is formed of a white LED, for example. Pulsed white light illuminated by the light source device 9 passes through the connector 7 and the universal cord 6 to become illumination light radiated from the distal end of the insertion unit 4 of the endoscope 2 toward a subject.

The processor 10 performs predetermined image processing on the image signal output from the connector 7 and controls the entire endoscope apparatus 1. The display device 13 displays the image signal processed by the processor 10.

An operating unit 5 provided with various buttons and knobs to operate an endoscopic function is connected to a proximal end side of the insertion unit 4 of the endoscope 2. The operating unit 5 is provided with a treatment tool insertion port 17 from which a treatment tool such as forceps, an electric knife, or an examination probe is inserted into the body cavity of the subject.

The insertion unit 4 is formed of the distal end portion 31 provided with the imaging apparatus, a bend portion 32 that is continuously connected to a proximal end side of the distal end portion 31 and freely bent in a plurality of directions, and a flexible tube 33 that is continuously connected to a proximal end side of the bend portion 32. The bend portion 32 is bent by an operation on a bend operation knob provided in the operating unit 5, and is freely bent in four directions including upward, downward, left and right directions according to traction and slackening of a bend wire inserted through the interior of the insertion unit 4.

A light guide bundle (not shown) transmitting the illumination light from the light source device 9 is arranged in the endoscope 2, and an illumination lens (not shown) is arranged at an end to which the illumination light from the light guide bundle is emitted. The illumination lens is provided at the distal end portion 31 of the insertion unit 4 so that the illumination light is radiated toward the subject.

Figure 2:
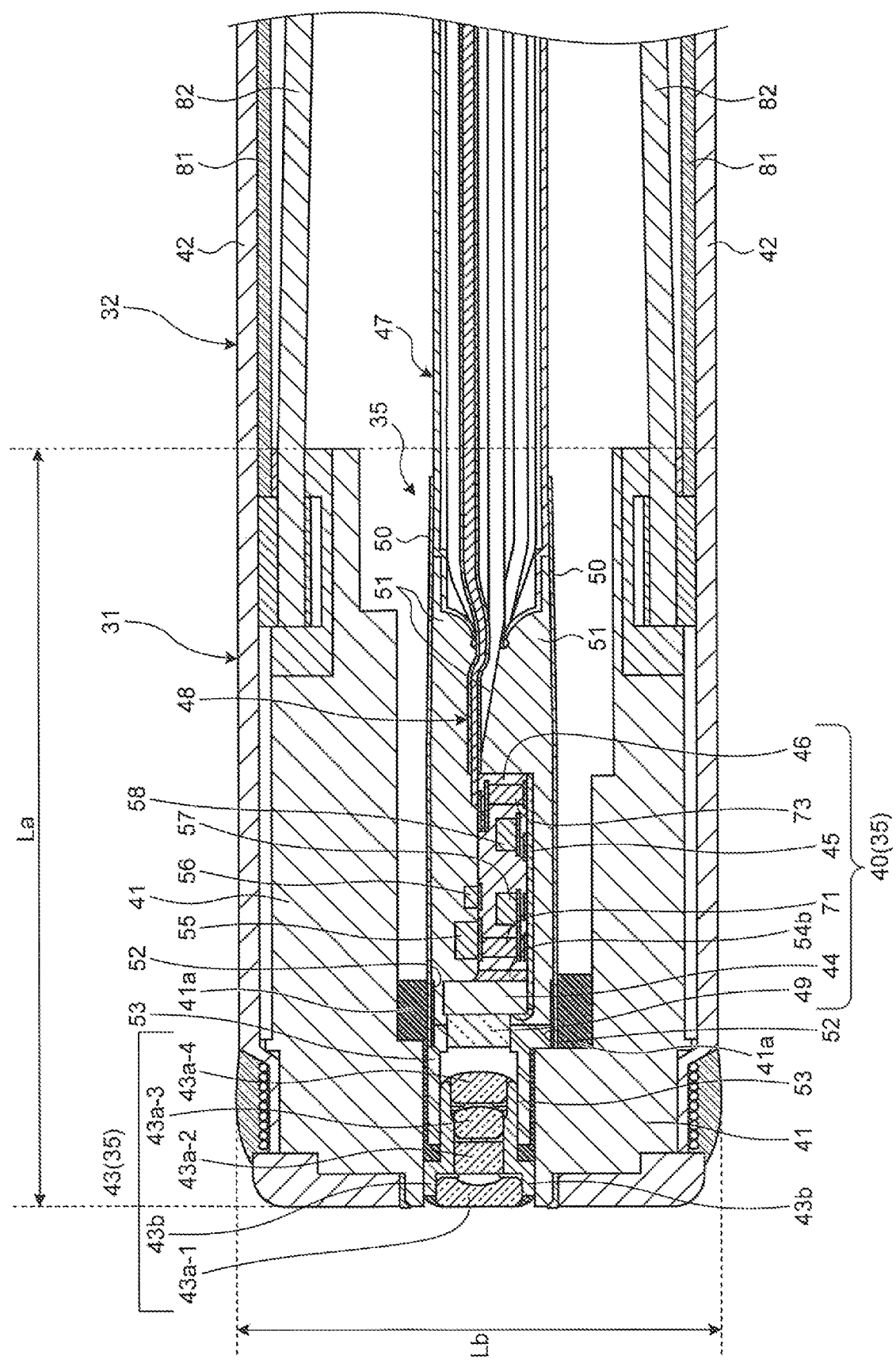
FIG. 2 is a partial cross-sectional view of a distal end of an endoscope illustrated in FIG. 1.

Next, the configuration of the distal end portion 31 of the endoscope 2 will be described in detail. FIG. 2 is a partial cross-sectional view of the distal end of the endoscope 2. FIG. 2 is a cross-sectional view obtained when the distal end is sectioned by a plane that is orthogonal to a substrate surface of an imaging unit provided at the distal end portion 31 of the endoscope 2 and is parallel to an optical axis direction of the imaging unit. FIG. 2 illustrates the distal end portion 31 and a part of the bend portion 32 of the insertion unit 4 of the endoscope 2.

As illustrated in FIG. 2, the bend portion 32 is freely bent in the four directions including the upward, downward, left and right directions according to traction and slackening of a bend wire 82 inserted through the interior of a bend tube 81 that is arranged on the inner side of a cover tube 42 to be described. An imaging apparatus 35 is provided inside the distal end portion 31 extending on the distal end side of the bend portion 32.

The imaging apparatus 35 includes a lens unit 43 and an imaging unit 40 arranged on the proximal end side of the lens unit 43, and adheres to the inner side of a distal end body 41 by an adhesive 41a. The distal end body 41 is made of a rigid member that forms an inner space that accommodates the imaging apparatus 35. The outer periphery of the proximal end of the distal end body 41 is covered by the flexible cover tube 42. A member arranged on the proximal end side relative to the distal end body 41 is formed of a flexible member to allow the bend portion 32 to be bent. The distal end portion 31 where the distal end body 41 is arranged corresponds to a rigid portion of the insertion unit 4. A length La of the rigid portion corresponds to the length from the distal end of the insertion unit 4 to the proximal end of the distal end body 41. Note that a length Lb corresponds to an outer diameter of the distal end of the insertion unit 4.

The lens unit 43 includes a plurality of objective lenses 43a-1 to 43a-4 and a lens holder 43b holding the objective lenses 43a-1 to 43a-4, where a distal end of the lens holder 43b is fixed to the distal end body 41 by fitted and fixed to the interior of the distal end body 41.

The imaging unit 40 includes a solid state image sensor 44 such as a CCD or CMOS which generates an electrical signal by performing photoelectric conversion on light received, an FPC board 45 (hereinafter referred to as an "FPC board 45") which extends in the optical axis direction from the solid state image sensor 44, a multi-layer substrate 46 which includes a plurality of conductor layers formed on a surface of the FPC board 45, and a glass lid 49 which adheres to the solid state image sensor 44 while covering a light-receiving surface of the solid state image sensor 44. On or in the multi-layer substrate 46 of the imaging unit 40, electronic components 55 to 58 are mounted that constitute a drive circuit of the solid state image sensor 44. The multi-layer substrate 46 includes via holes 71 and 73 to establish electrical conduction among the plurality of conductor layers. Moreover, a distal end of each signal cable 48 of an electric cable bundle 47 is connected to a proximal end of the multi-layer substrate 46. An electronic component other than the electronic components constituting the drive circuit of the solid state image sensor 44 may be mounted on or in the multi-layer substrate 46 as well.

A proximal end of each signal cable 48 extends in a proximal end direction of the insertion unit 4. The electric cable bundle 47 is inserted/arranged in the insertion unit 4 and extends up to the connector 7 through the operating unit 5 and the universal cord 6 illustrated in FIG. 1.

A subject image formed by the objective lenses 43*a*-1 to 43*a*-4 of the lens unit 43 is detected by the solid state image sensor 44 arranged at image-forming positions of the objective lenses 43*a*-1 to 43*a*-4 and converted into the imaging signal. The imaging signal is output to the processor 10 via the signal cable 48 connected to the FPC board 45 and the multi-layer substrate 46 as well as the connector 7.

The solid state image sensor 44 adheres to the FPC board 45 and the multi-layer substrate 46. The solid state image sensor 44 and a connection portion between the solid state image sensor 44 and the FPC board 45 are covered by a metallic reinforcing member 52. In order to prevent the influence of external static electricity against the electronic components 55 to 58 on the FPC board 45, the reinforcing member 52 is installed away from the solid state image sensor 44, the FPC board 45 and the multi-layer substrate 46.

An outer periphery of a distal end portion of each of the imaging unit 40 and the electric cable bundle 47 is covered by a heat-shrinkable tube 50 in order to increase tolerance. An adhesive resin 51 fills a gap among components inside the heat-shrinkable tube 50.

A solid state image sensor holder 53 holds the solid state image sensor 44 adhering to the glass lid 49 by fitting an outer peripheral surface of the glass lid 49 into an inner peripheral surface on the proximal end side of the solid state image sensor holder 53. An outer peripheral surface on the proximal end side of the solid state image sensor holder 53 is fitted to an inner peripheral surface on the distal end side of the reinforcing member 52. An outer peripheral surface on the proximal end side of the lens holder 43*b* is fitted to an inner peripheral surface on the distal end side of the solid state image sensor holder 53. While each member is fitted in this manner, the outer peripheral surface of the lens holder 43*b,* the outer peripheral surface of the solid state image sensor holder 53 and an outer peripheral surface on the distal end side of the heat-shrinkable tube 50 are fixed to an inner peripheral surface of the distal end of the distal end body 41 by the adhesive 41*a*.

Figure 3:
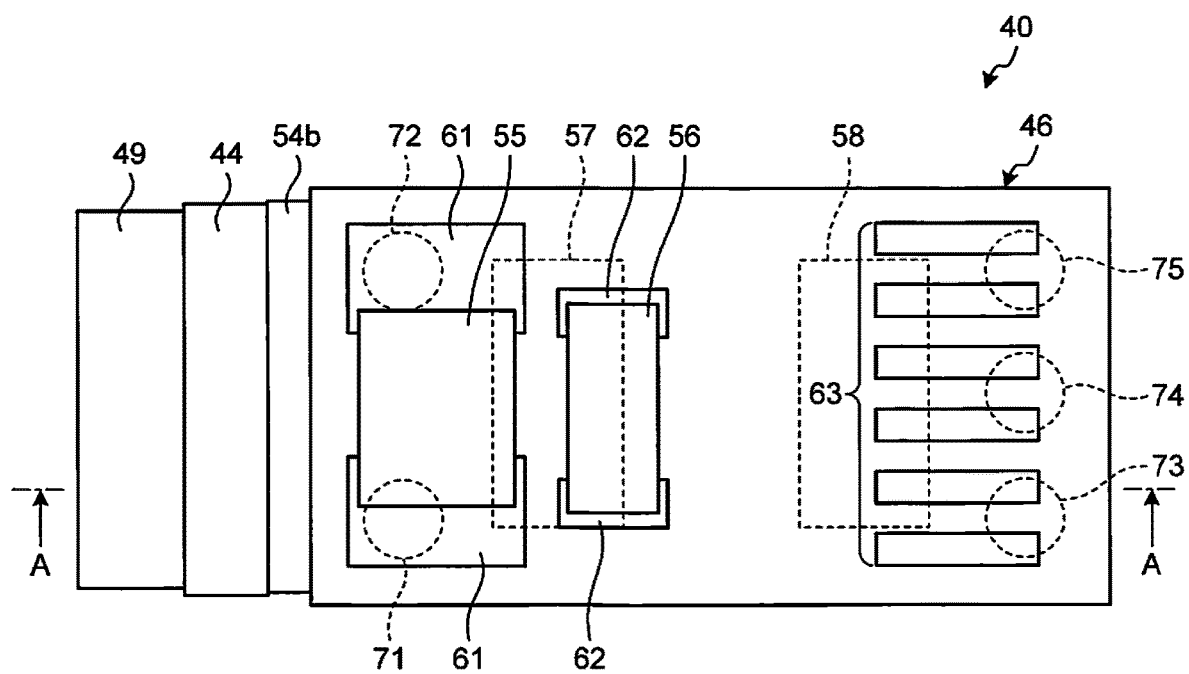
FIG. 3 is a plan view of an imaging unit illustrated in FIG. 2 as seen in planar view along a layered direction.
Figure 4:
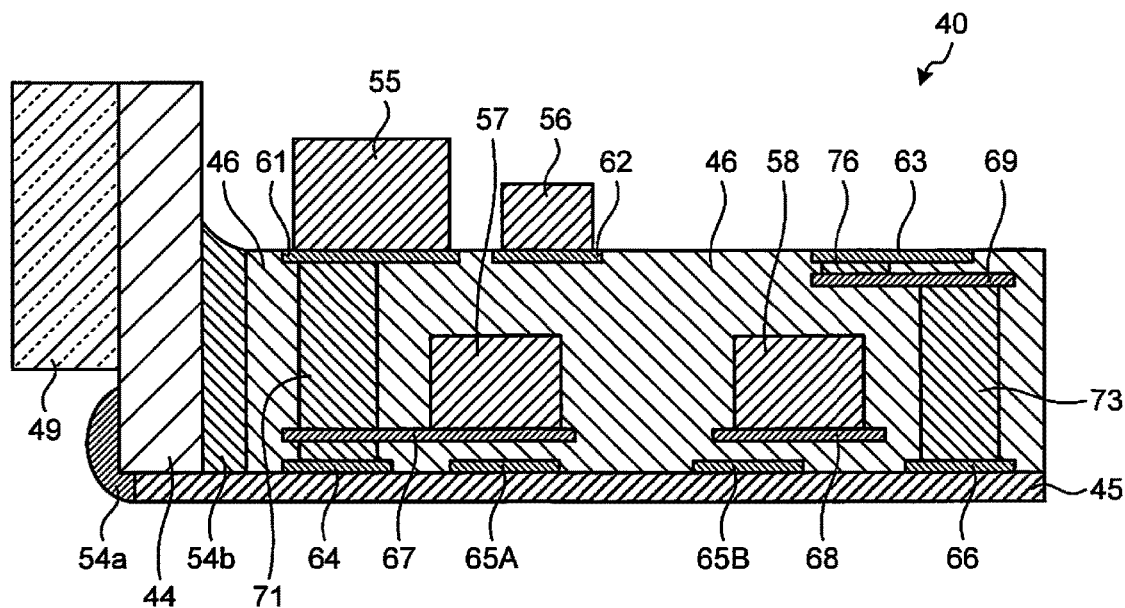
FIG. 4 is a cross-sectional view taken along line A-A of FIG. 3.

The imaging unit 40 will now be described. FIG. 3 is a plan view of the imaging unit 40 as seen in planar view along a layered direction. FIG. 4 is a cross-sectional view taken along line A-A of FIG. 3 and obtained when the imaging unit 40 is sectioned by a plane perpendicular to the surface of the FPC board 45 and parallel to the optical axis direction of the solid state image sensor 44.

The FPC board 45 extends toward the optical axis direction of the solid state image sensor 44 from a side opposite to the light-receiving surface of the solid state image sensor 44. The multi-layer substrate 46 formed by stacking a plurality of layers is formed on the surface of the FPC board 45 and is electrically and mechanically connected to the FPC board 45. A back side of the solid state image sensor 44 and a side face of the multi-layer substrate 46 on the side of the solid state image sensor adhere to each other by an adhesive 54*b*. The FPC board 45 will be described in detail later on.

Among the plurality of electronic components 55 to 58 constituting the drive circuit of the solid state image sensor 44, one or more electronic components are mounted on a top surface of the multi-layer substrate 46 while one or more other electronic components are embedded inside the multi-layer substrate 46. FIGS. 3 and 4 illustrate an example where, among the plurality of electronic components 55 to 58, the two electronic components 55 and 56 are mounted on the top surface of the multi-layer substrate 46. Also, among the plurality of electronic components 55 to 58, the two electronic components 57 and 58 are embedded inside the multi-layer substrate 46.

Formed on the multi-layer substrate 46 are two connection lands 61 to which the electronic component 55 is electrically connected, two connection lands 62 to which the electronic component 56 is connected, and a cable connection land 63 to which a conductor at the distal end of the signal cable 48 is electrically and mechanically connected. FIG. 3 illustrates an example where six cable connection lands 63 are provided to allow six signal cables 48 to be connected to the lands through solder or the like. A plurality of connection lands 64, 65A, 65B and 66 electrically connected to the FPC board 45 is formed on a bottom surface of the multi-layer substrate 46.

A plurality of conductor layers is stacked inside the multi-layer substrate 46. Conductor layers 67, 68 and 69 are illustrated in the cross section in FIG. 4. Moreover, a plurality of via holes 71 to 76 is formed inside the multi-layer substrate 46. Each of the plurality of conductor layers including the conductor layers 67 to 69 is formed to be electrically connected to any of the plurality of via holes 71 to 76.

As illustrated in FIG. 4, the electronic components 57 and 58 embedded inside the multi-layer substrate 46 are mounted on the conductor layers 67 and 68, respectively, which are second layers from the outermost layer being the bottom surface of the multi-layer substrate 46. When the electronic component is mounted or embedded on or in the conductor layer formed in the outermost layer (such as a layer at the same level as the connection lands 64, 65A, 65B and 66 or a layer at the same level as the connection lands 61 and 62), the electronic components 57 and 58 are possibly disconnected by heat generated in mounting the electronic components 55 and 56 and connecting the signal cable 48 to the surface of the multi-layer substrate 46 or connecting the FPC board 45 and the multi-layer substrate 46, whereby the conductor layers 67 and 68 to which the electronic components 57 and 58 are connected are preferably formed on the second layer or inward from the outermost layer. The thickness of the multi-layer substrate 46 is increased when the conductor layers are formed on a third layer or inward so that, in order to achieve connection reliability and reduce the thickness of the multi-layer substrate 46, the conductor layers are more preferably formed on the second layer from the outermost layer.

Figure 5:
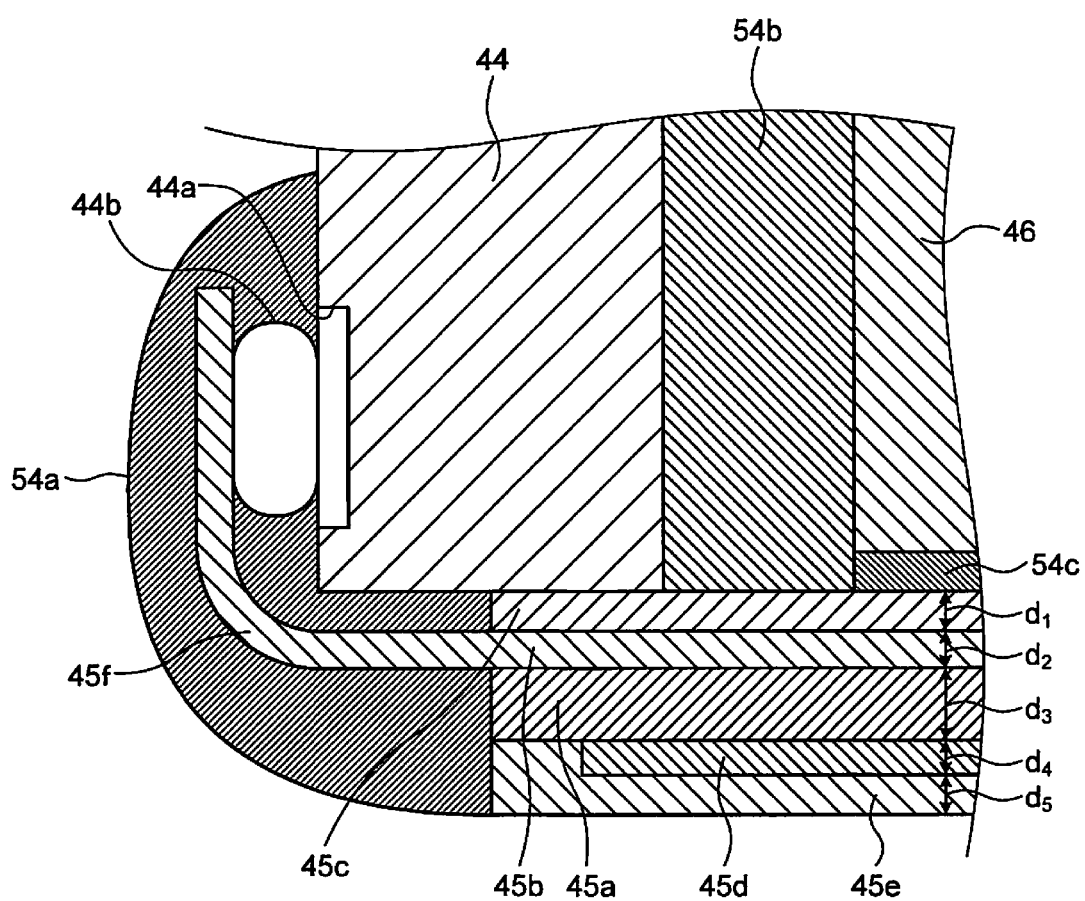
FIG. 5 is an enlarged view of a part of the imaging unit illustrated in FIG. 4.

FIG. 5 is an enlarged view of the connection portion between the solid state image sensor 44 and the FPC board 45 of the imaging unit 40 illustrated in FIG. 4. The FPC board 45 includes an insulating base material 45*a,* a first surface-side wiring layer 45*b* formed on the side of a first surface of the base material 45*a* nearer the solid state image sensor 44, a first surface-side electrical insulating film 45c insulating the first surface-side wiring layer 45b, a second surface-side wiring layer 45d formed on the side of a second surface of the base material 45a being a back side of the first surface nearer the solid state image sensor 44, and a second surface-side electrical insulating film 45e insulating the second surface-side wiring layer 45d. The FPC board 45 further includes an inner lead 45f that is connected to an electrode pad (not shown) formed in the solid state image sensor 44 and is formed from the first surface-side wiring layer 45b. It is preferable that a wiring pattern on the first surface side, a connection land to be connected to the multi-layer substrate 46 and an alignment recognition mark used in connecting the multi-layer substrate 46 are formed on the first surface-side wiring layer 45b. By using the recognition mark provided in the first surface-side wiring layer 45b to perform alignment at the time of connecting the multi-layer substrate, the position of the multi-layer substrate relative to the connection portion of the solid state image sensor 44 and the inner lead 45f varies less. Moreover, the first surface-side electrical insulating film 45c is made open at a position corresponding to the recognition mark, whereby the accuracy of recognition can be increased.

The inner lead 45f is bent about 90° along the side of the light-receiving surface of the rectangular parallelepiped solid state image sensor 44 from the side face thereof, and is electrically connected to an electrode pad 44a formed on the side of the light-receiving surface of the solid state image sensor 44 through a bump 44b or the like. The periphery of a connection portion between the inner lead 45f and the electrode pad 44a is covered by an insulating sealing resin 54a.

Figure 6:
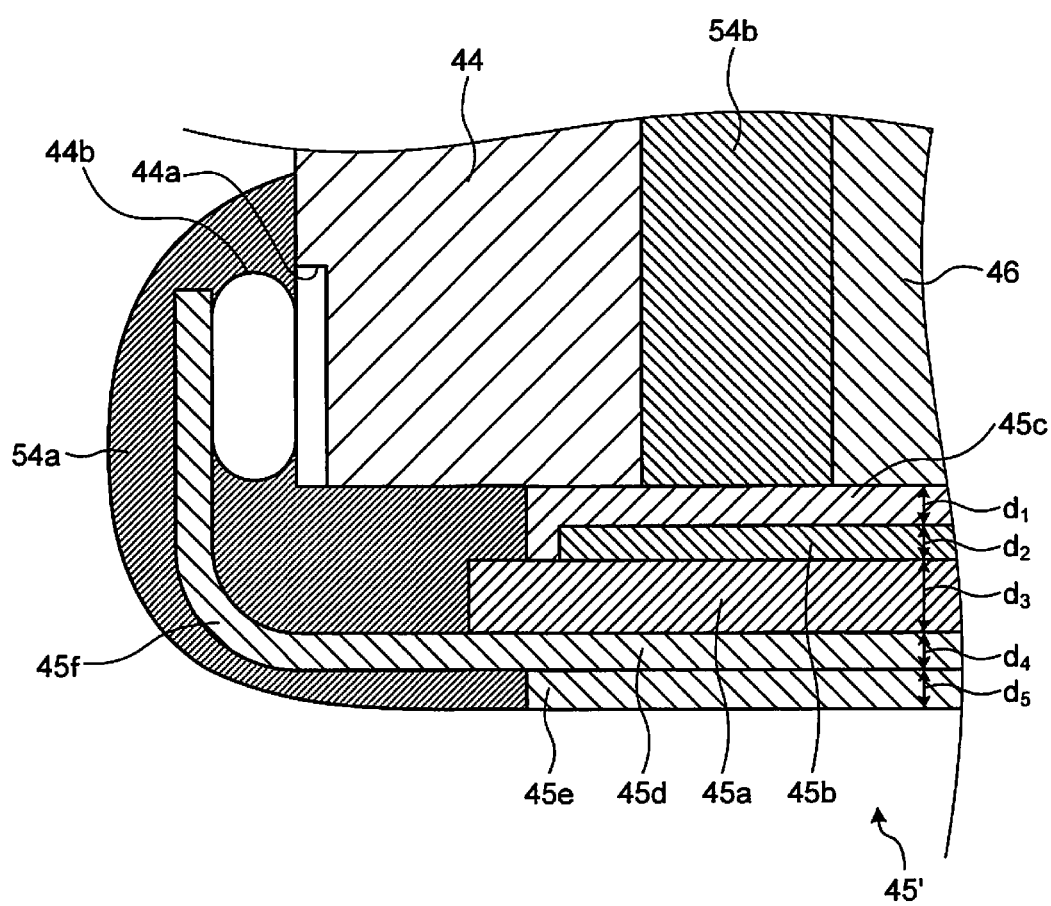
FIG. 6 is a cross-sectional view illustrating an example of a conventional flexible printed circuit board.

FIG. 6 illustrates a cross-sectional view of a conventional FPC board. A conventional FPC board 45' is adapted such that an inner lead 45f is formed from a second surface-side wiring layer 45d, and a base material 45a is located in a direction in which the inner lead 45f is bent. In the FPC board 45 and the FPC board 45' having a layered structure, there is a variation in layer thicknesses d1, d2, d3, d4, and d5. The length of the inner lead 45f is determined in consideration of a distance from the inner lead 45f to the side face of the solid state image sensor 44, a position at which each of the FPC boards 45, 45' and the solid state image sensor 44 are connected, and a position (height) of the electrode pad 44a of the solid state image sensor 44, where the inner lead 45f becomes shorter or longer than a predetermined length when the distance from the inner lead 45f to the side face of the solid state image sensor 44 varies considerably so that connection to the electrode pad 44a becomes less reliable in some cases. While the variation in the distance from the inner lead 45f to the side face of the solid state image sensor 44 is caused by only the thickness d1 of the first surface-side electrical insulating film 45c in the first embodiment, the variation increases in a conventional example as the variation is caused by the thicknesses d1+d2+d3 of the base material 45a, the first surface-side wiring layer 45b and the first surface-side electrical insulating film 45c added together so that the connection possibly becomes less reliable. In the first embodiment, the variation in the distance from the inner lead 45f to the side face of the solid state image sensor 44 can be decreased to thus be able to maintain the connection reliability.

Moreover, in the first embodiment, the inner lead 45f is bent about 90° along the side of the light-receiving surface of the solid state image sensor 44 from the side face thereof and connected to the electrode pad 44a, so that the inner lead does not easily bulge out when bent to thus be able to prevent an increase in size of the imaging unit 40. Furthermore, the multi-layer substrate 46 is connected to a connection land of the first surface-side wiring layer 45b from which the inner lead 45f extends, so that a relative position between the connection portion of the inner lead 45f and the electrode pad 44a and the multi-layer substrate 46 varies less and, as a result, the imaging unit 40 can have a decreased width and a shorter rigid portion to thus be reduced in size. Conversely, when the inner lead 45f is formed of the extension from the second surface-side wiring layer 45d as with the conventional example, the position gap between the first surface-side wiring layer 45b and the second surface-side wiring layer 45d causes the increase in variation of the relative position between the connection portion of the inner lead 45f and the electrode pad 44a and the multi-layer substrate 46.

Figure 7:
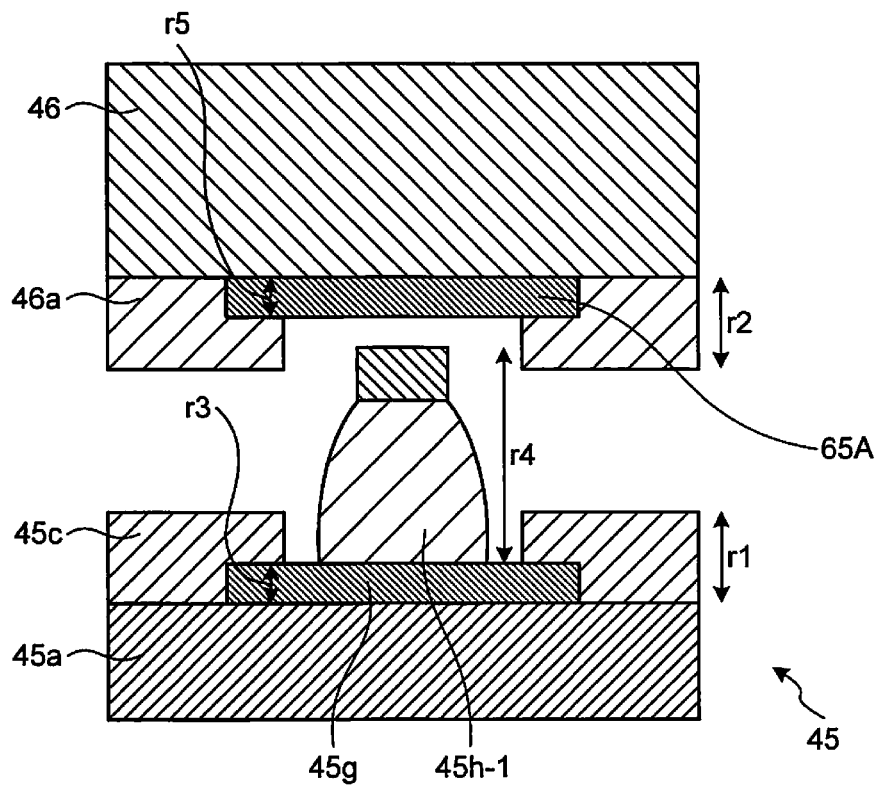
FIG. 7 is a cross-sectional view illustrating a connection portion between an FPC board and a multi-layer substrate.

Note that the FPC board 45 and the multi-layer substrate 46 are connected by a bump in the first embodiment. FIG. 7 is an enlarged cross-sectional view illustrating a connection portion between a connection land 65A of the multi-layer substrate 46 and a connection land 45g of the FPC board 45. The connection land 65A of the multi-layer substrate 46 and the connection land 45g of the FPC board 45 are electrically connected by a bump 45h-1 such as an Au stud bump or a solder bump. The surface excluding the connection portion of the connection land 65A of the multi-layer substrate 46 is covered by an insulating film 46a such as a solder resist, whereas the surface excluding the connection portion of the connection land 45g of the FPC board 45 is covered by a first surface-side electrical insulating film 45c such as a solder resist. In order to increase the connection reliability in the connection portion, the sum of a thickness r1 of the first surface-side electrical insulating film 45c and a thickness r2 of the insulating film 46a is preferably smaller than the sum of a thickness r3 of the connection land 45g, a height r4 of the bump 45h-1 and a thickness r5 of the connection land 65A.

Figure 8:
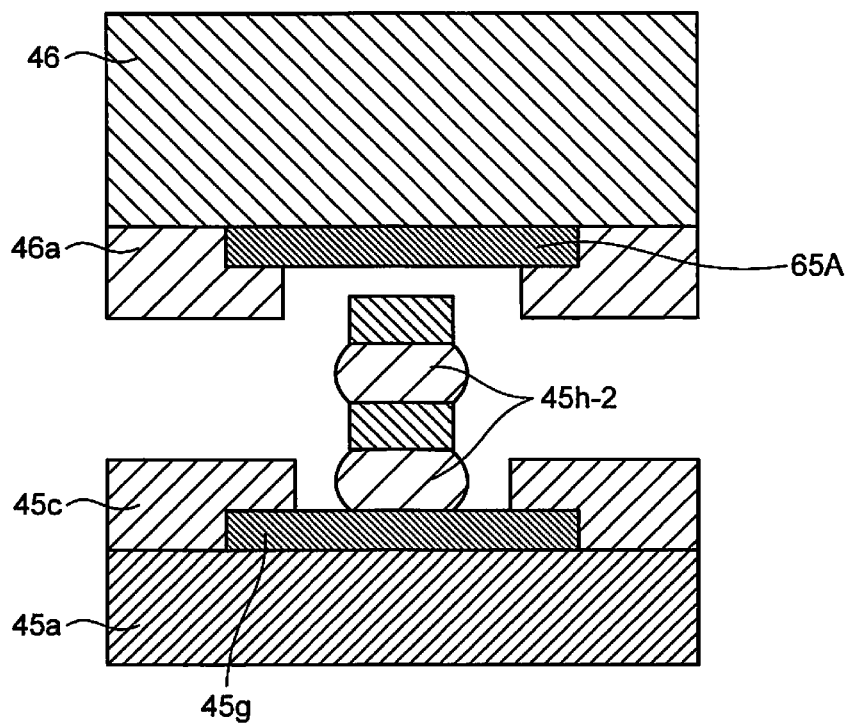
FIG. 8 is a cross-sectional view illustrating a connection portion between the FPC board and the multi-layer substrate.
Figure 9:
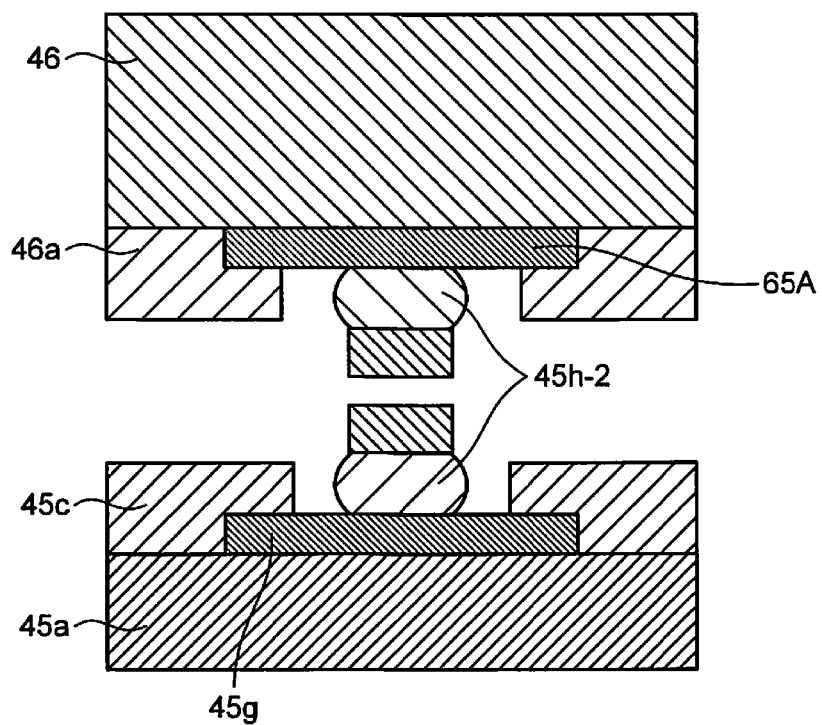
FIG. 9 is a cross-sectional view illustrating a connection portion between the FPC board and the multi-layer substrate.

Alternatively, as illustrated in FIGS. 8 and 9, the bump used in connection may be employed in a way that two bumps 45h-2 that are small in height are placed on top of each other, or the bump 45h-2 small in height is disposed on each of the connection land 45g and the connection land 65A. When using the bump 45h-2 illustrated in FIGS. 8 and 9 as well, the sum of the thickness of the first surface-side electrical insulating film 45c and the thickness of the insulating film 46a is preferably smaller than the sum of the thickness of the connection land 45g, the total height of the bump 45h-2 and the thickness of the connection land 65A.

In the first embodiment, a connector terminal 37 used for examination is formed on an FPC board 45A (refer to FIG. 10) before cut-out in order to inspect an electrical property at the time of connecting the FPC board 45 and the solid state image sensor 44 and connecting the FPC board 45 and the multi-layer substrate 46. The number of the connector terminals 37 corresponds to the number of the inner leads 45f, and the electrical property is inspected by bringing a terminal of an examination device into contact with the connector terminal 37. The connector terminal 37 can also be formed outside a product area indicated with a dotted line in FIG. 10 to extract an output signal of the electronic component mounted on or in the multi-layer substrate 46. In a manufacturing process of the imaging unit 40, the connector terminal 37 is used to be able to inspect connection quality in each process after connecting the inner lead 45f of the FPC board 45 and the electrode pad of the solid state image sensor 44 (INNER LEAD BONDING: ILB), whereby a defective product can be detected early to thus be able to decrease a manufacturing cost.

Figure 10:
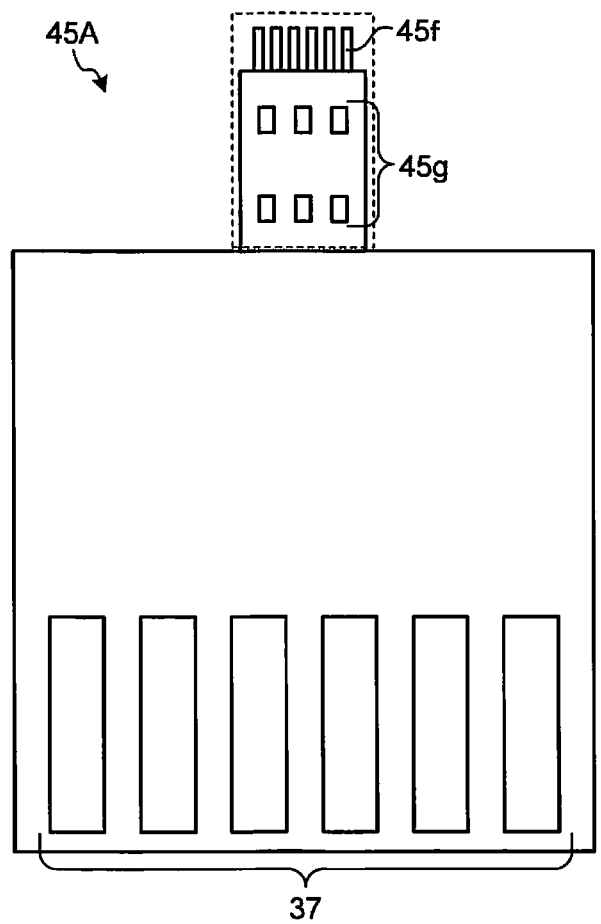
FIG. 10 is a diagram illustrating the FPC board before a use area is cut out.

The FPC board 45A before cutting out a use area is connected to the multi-layer substrate 46 and the solid state image sensor 44 and thereafter cut in a connection area indicated with the dotted line in FIG. 10. The FPC board 45A is conventionally cut at a predetermined cut position on the FPC board 45A where, when there is a large gap in the connection position between the FPC board 45A and the multi-layer substrate 46, the FPC board sometimes cannot be cut at the predetermined cut position or, when cut at the predetermined cut position, the outer shape of the imaging unit 40 is sometimes increased in size.

Figure 11:
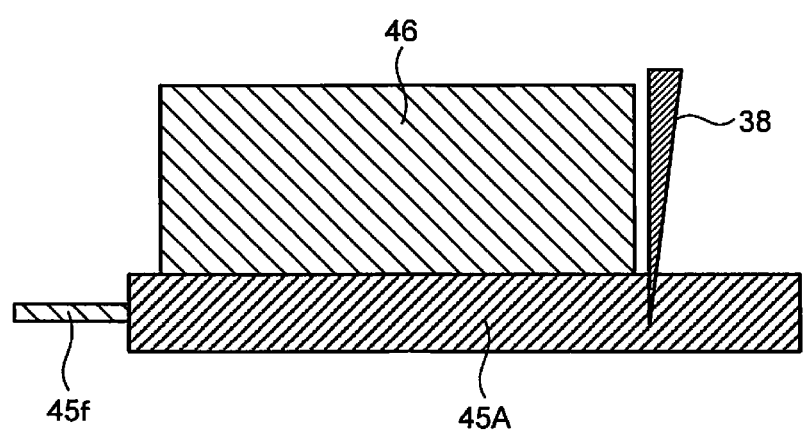
FIG. 11 is a diagram illustrating cutting of the FPC board illustrated in FIG. 10.
Figure 12:
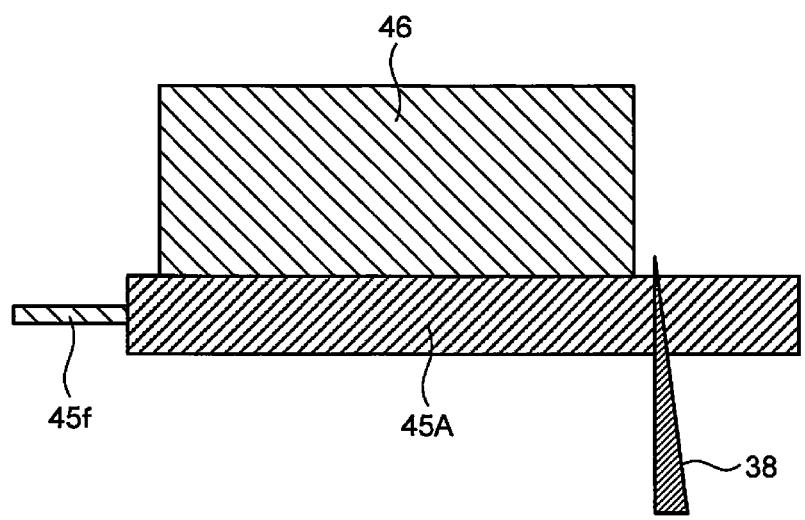
FIG. 12 is a diagram illustrating cutting of the FPC board illustrated in FIG. 10.
Figure 13:
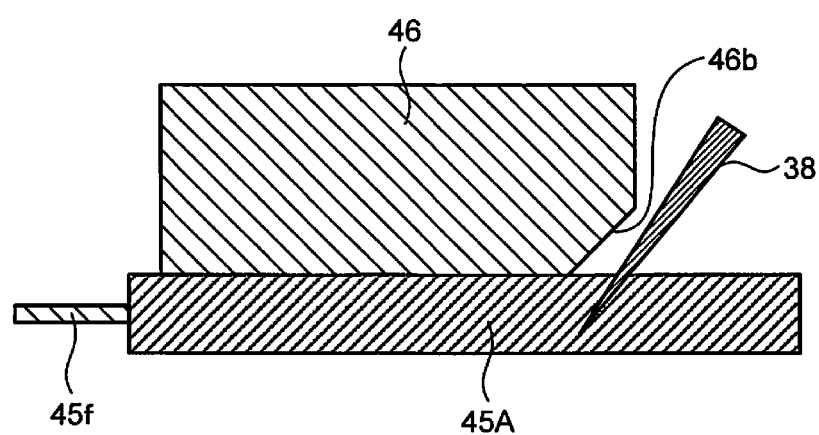
FIG. 13 is a diagram illustrating cutting of the FPC board illustrated in FIG. 10.

Accordingly, as illustrated in FIGS. 11 to 13, the FPC board 45A is preferably cut with reference to the outer shape of the multi-layer substrate 46. The FPC board 45A may be cut by placing a cutting tool 38 along the multi-layer substrate 46 from the side of the multi-layer substrate 46 (refer to FIG. 11), placing the cutting tool 38 along the outer shape of the multi-layer substrate 46 seen through the FPC board from the side of the FPC board 45A (refer to FIG. 12), or forming a chamfered portion 46b at a bottom face of the multi-layer substrate 46, placing the cutting tool 38 along the chamfered portion 46b and cutting the FPC board 45A at a position inside the outer shape of the multi-layer substrate 46 (refer to FIG. 13).

While there has been described the imaging unit 40 in which the multi-layer substrate 46 incorporating the electronic components 57 and 58 is connected to the FPC board 45 in the first embodiment, an effect similar to that of the first embodiment can also be obtained when one or more electronic components are directly mounted on the FPC board 45 or when a cavity-formed rigid substrate 60 having a recess (cavity) in which an electronic component is mounted is connected to the FPC board.

Figure 14:
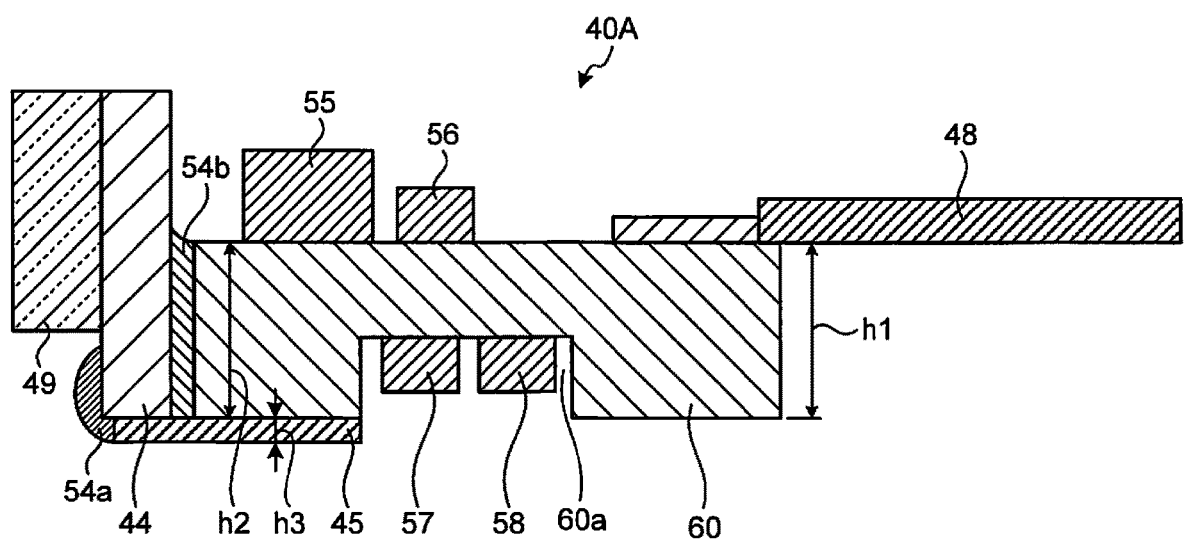
FIG. 14 is a side view of an imaging unit according to a modification of a first embodiment.

FIG. 14 is a side view of an imaging unit according to a modification of the first embodiment. According to an imaging unit 40A of the modification, the cavity-formed rigid substrate 60 is connected to an FPC board 45. Electronic components 57 and 58 are mounted in a cavity 60a of the cavity-formed rigid substrate 60. In the imaging unit 40A of the modification, the cavity 60a is preferably formed not at a rear end (end at which a signal cable 48 is connected) but at a center of the cavity-formed rigid substrate 60 in order to improve workability in connecting the signal cable 48 to a top surface of the cavity-formed rigid substrate 60. Moreover, a height h1 of the rear end of the cavity-formed rigid substrate 60 is preferably roughly equal to the sum of a height h2 of a front end of the substrate and a thickness h3 of the FPC board 45 but, when the thickness h3 of the FPC board 45 is small, the height h1 of the rear end of the cavity-formed rigid substrate 60 may be formed to equal the height h2 of the front end. Such configuration allows the imaging unit 40A to be received and fixed on a flat surface at the time of soldering the cable 48, thereby facilitating the soldering work. The similar effect can be achieved when a bottom surface side of the imaging unit 40 is flat as with the first embodiment.

Second Embodiment

Figure 15:
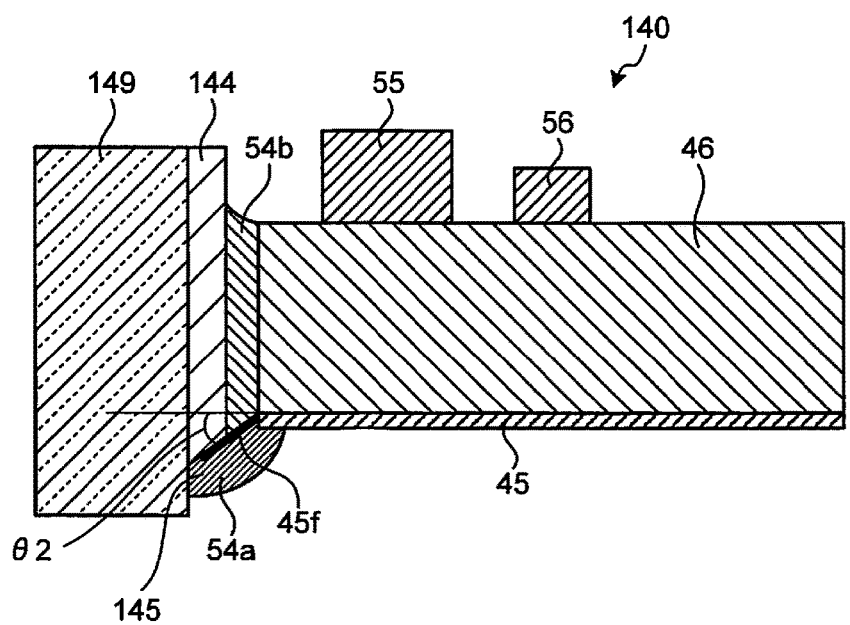
FIG. 15 is a side view of an imaging unit according to a second embodiment.
Figure 16:
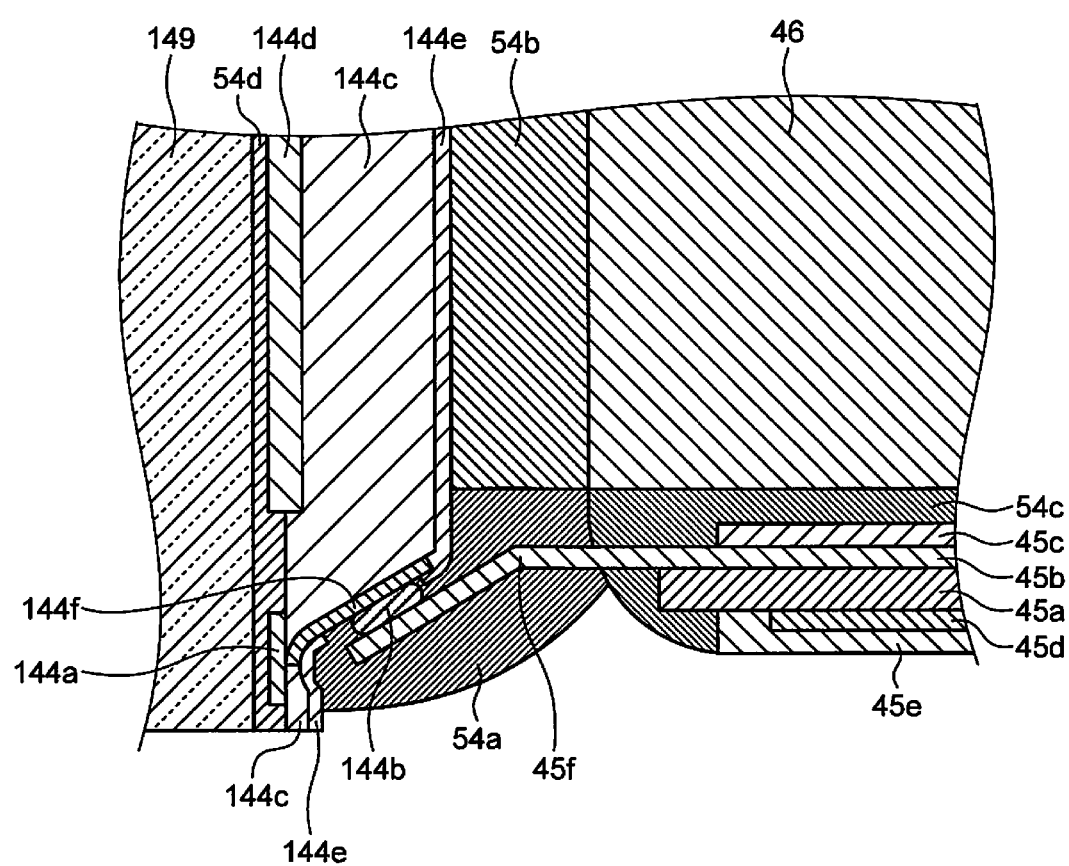
FIG. 16 is an enlarged cross-sectional view of a connection portion between a solid state image sensor and an FPC board of the imaging unit illustrated in FIG. 15.

An imaging unit according to a second embodiment is different from the first embodiment in that a solid state image sensor includes an oblique electrode, to which an inner lead of an FPC board is connected. FIG. 15 is a side view of the imaging unit according to the second embodiment. FIG. 16 is an enlarged cross-sectional view of a connection portion between the solid state image sensor and the FPC board of the imaging unit illustrated in FIG. 15.

In an imaging unit 140 according to the second embodiment, a solid state image sensor 144 includes a notch 145 from which an electrode pad 144a is exposed to the side of an FPC board 45. The notch 145 is formed to traverse the surface of the solid state image sensor 144 on the side of the FPC board 45 so that a plurality of electrode pads 144a is exposed to the side of the FPC board 45. The notch 145 is a slope formed at a predetermined angle with a light-receiving unit 144d by chemical or physical etching or mechanical cutting.

The solid state image sensor 144 and a glass lid 149 adhere to each other by a bonding layer 54d made of a transparent adhesive or the like. Moreover, a protective film 144e is formed on a surface of a back side of the light-receiving unit 144d of a body 144c.

An oblique electrode 144f connected to the electrode pad 144a is formed on the slope of the notch 145, and an inner lead 45f of the FPC board 45 is electrically connected to the oblique electrode 144f through a bump 144b. A connection portion between the inner lead 45f and the oblique electrode 144f is sealed by a sealing resin 54a. The notch 145 is formed so as to house the sealing resin 54a in the notch 145, thereby preventing an increase in size of the imaging unit due to the sealing resin 54a sticking out. Moreover, an adhesive 54c reinforcing an interface between the FPC board 45 and a multi-layer substrate 46 seeps toward the inner lead, the base of which is then reinforced to be able to prevent deformation of the inner lead.

Figure 17:
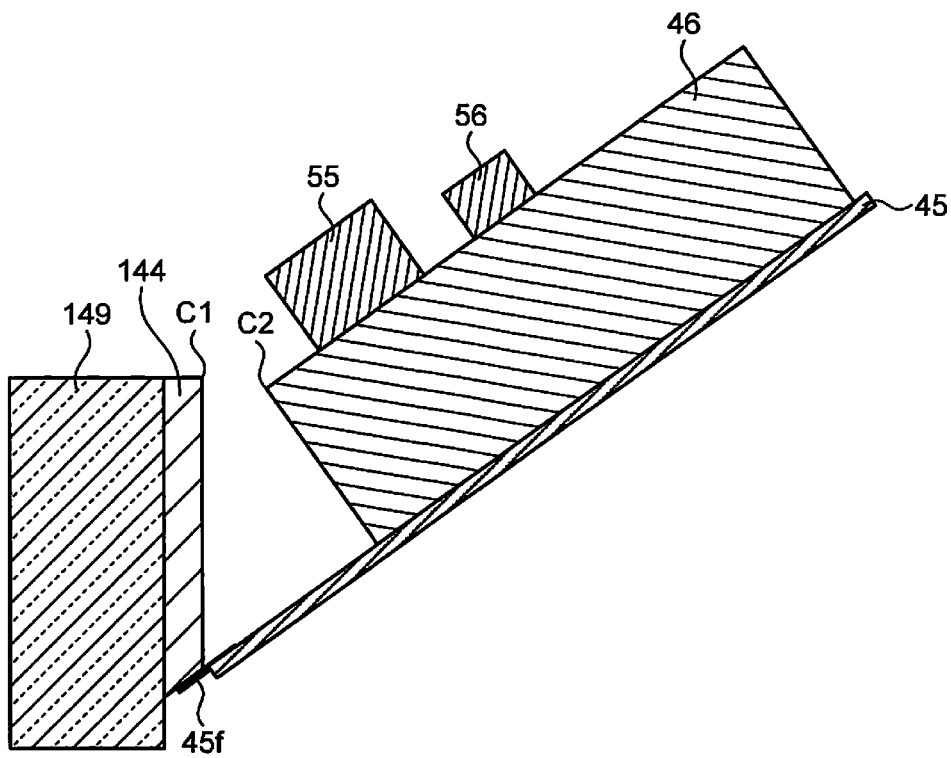
FIG. 17 is a diagram illustrating an undesirable example of a method of manufacturing the imaging unit according to the second embodiment.

When the inner lead 45f extending from the FPC board 45 is directly connected in parallel with the oblique electrode 144f, the FPC board 45 needs to be extended in length in order to prevent interference between a corner C2 of the multi-layer substrate 46 and a corner C1 of the solid state image sensor 144 as illustrated in FIG. 17. In such case, the multi-layer substrate 46 and electronic components 55 and 56 lie outside a projected area on the surface orthogonal to an optical axis direction of the solid state image sensor 144, thereby hindering a diameter reduction of the imaging unit 140.

In order to reduce the diameter of the imaging unit 140, the inner lead 45f can be bent to fit the multi-layer substrate 46 and the electronic components 55 and 56 within the projected area projected in the optical axis direction of the solid state image sensor 144 but, as illustrated in FIG. 17, the length of a rigid portion of the imaging unit 140 (from the glass lid 149 to a rear end of the multi-layer substrate 46) is increased when the inner lead 45f is bent after connecting the FPC board 45 and the solid state image sensor 144.

Accordingly, the length of the rigid portion of the imaging unit 140 can be decreased while preventing interference between the solid state image sensor 144 and the multi-layer substrate 46 by bending the inner lead 45f at a predetermined angle and then connecting it to the oblique electrode 144f. The bend angle of the inner lead 45f is adjusted to an angle such that the FPC board 45 is parallel to the optical axis direction of the solid state image sensor 144 after connecting the inner lead 45f and the oblique electrode 144f.

Figure 18:
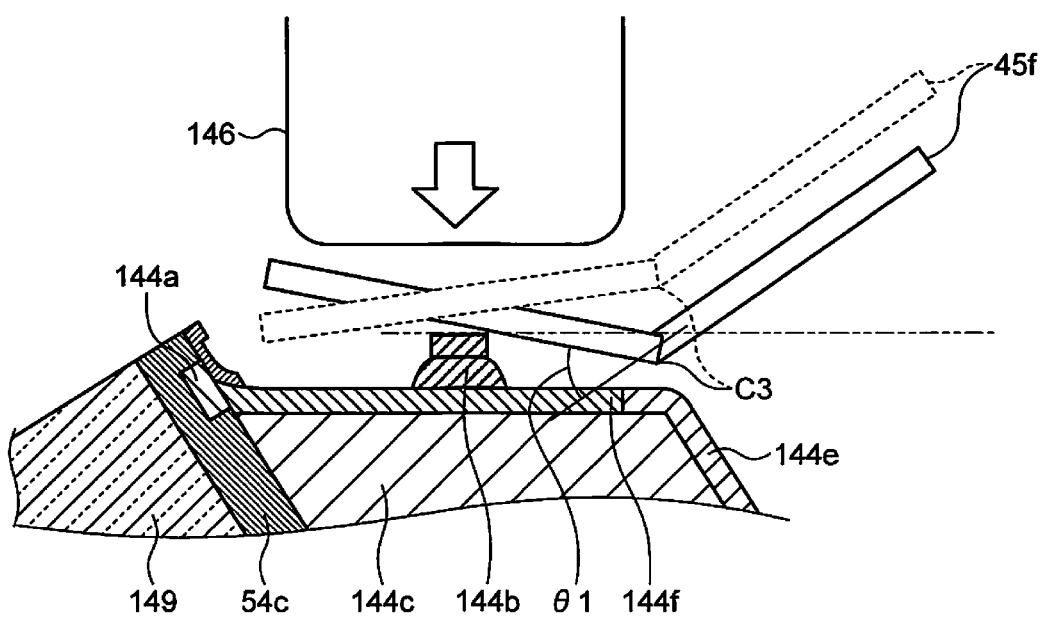
FIG. 18 is a cross-sectional view illustrating connection of an inner lead to an oblique electrode.

Note that a bend angle $\theta 1$ of the inner lead 45f is preferably set larger than a bend angle $\theta 2$ after connection. FIG. 18 is a cross-sectional view illustrating the connection of the inner lead 45f to the oblique electrode 144f.

The inner lead 45f is connected to the oblique electrode 144f while fixing the FPC board 45 by a tool and applying pressure to the connection portion by a bonding tool 146 where, when the bend angle $\theta 1$ is set smaller than or equal to the bend angle θ2 after connection (the inner lead indicated with a dotted line in FIG. 18), there is a possibility of a break in the lead because tensile stress applied to a lead bend C3 at the time of connection is larger than when the bend angle θ1 is set larger than the bend angle θ2 after connection (the inner lead indicated with a solid line in FIG. 18).

Figure 19:
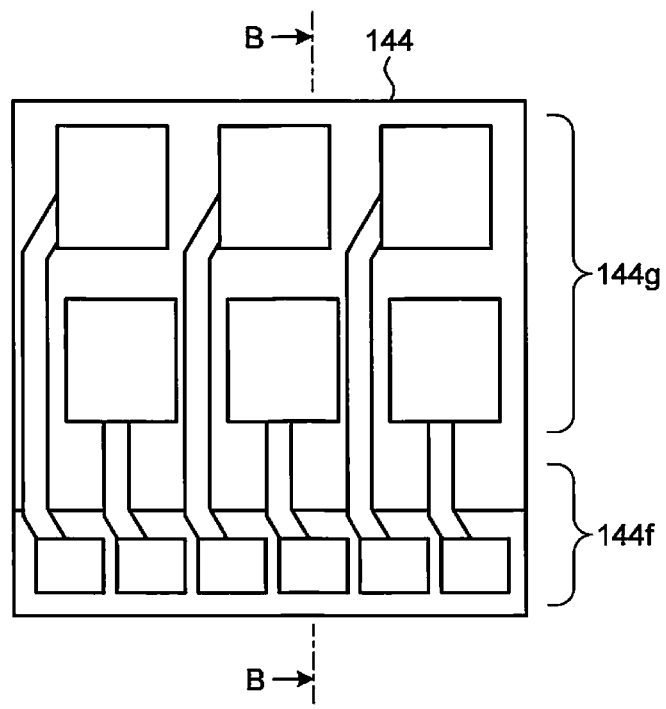
FIG. 19 is a diagram illustrating an examination pad and a bonding pad formed on a back side of a light-receiving surface of the solid state image sensor.
Figure 20:
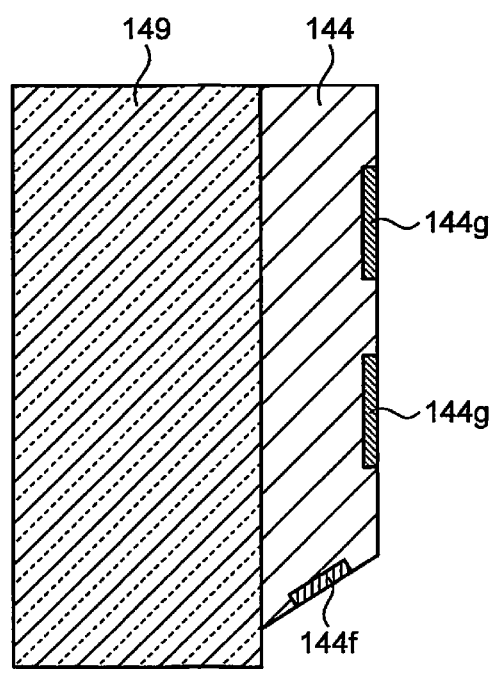
FIG. 20 is a cross-sectional view taken along line B-B of FIG. 19 illustrating the solid state image sensor.

Moreover, an examination pad for the solid state image sensor 144 is formed at a back side of the light-receiving unit 144d of the solid state image sensor 144. FIG. 19 is a diagram illustrating the examination pad formed at the back side of a light-receiving surface of the solid state image sensor 144, and FIG. 20 is a cross-sectional view taken along line B-B of FIG. 19 illustrating the solid state image sensor 144.

An examination pad 144g is formed at the back side of the solid state image sensor 144. When an examination is performed by bringing an examination probe into contact with the oblique electrode 144f without forming the examination pad 144g, a probe mark generated at the time of the examination is sometimes left on the oblique electrode. Flatness of the surface is deteriorated due to the probe mark when the bump 144b is formed on the oblique electrode on which the probe mark is left, whereby the bonding may possibly become less reliable. Accordingly, as illustrated in FIGS. 19 and 20, the examination pad 144g is preferably formed separately from the oblique electrode 144f. Note that a bonding pad different from the oblique electrode may be provided at the back side of the solid state image sensor 144 as well.

As with the first embodiment, according to the second embodiment, a connection land to which the multi-layer substrate is mounted is formed in a first surface-side wiring layer in which the inner lead is formed, so that a position gap between the connection portion of the inner lead and the connection position of the multi-layer substrate can be decreased to thus be able to prevent the increase in length of the rigid portion. Moreover, a base material of the FPC board is arranged at the back side of the inner lead to allow the height above the inner lead of the imaging unit to be decreased by the thickness of the base material, whereby a larger (taller) electronic component can be mounted within the projected area projected in the optical axis direction of the solid state image sensor. That is, the increase in size of the imaging unit can be prevented even when a tall electronic component is mounted.

Figure 21:
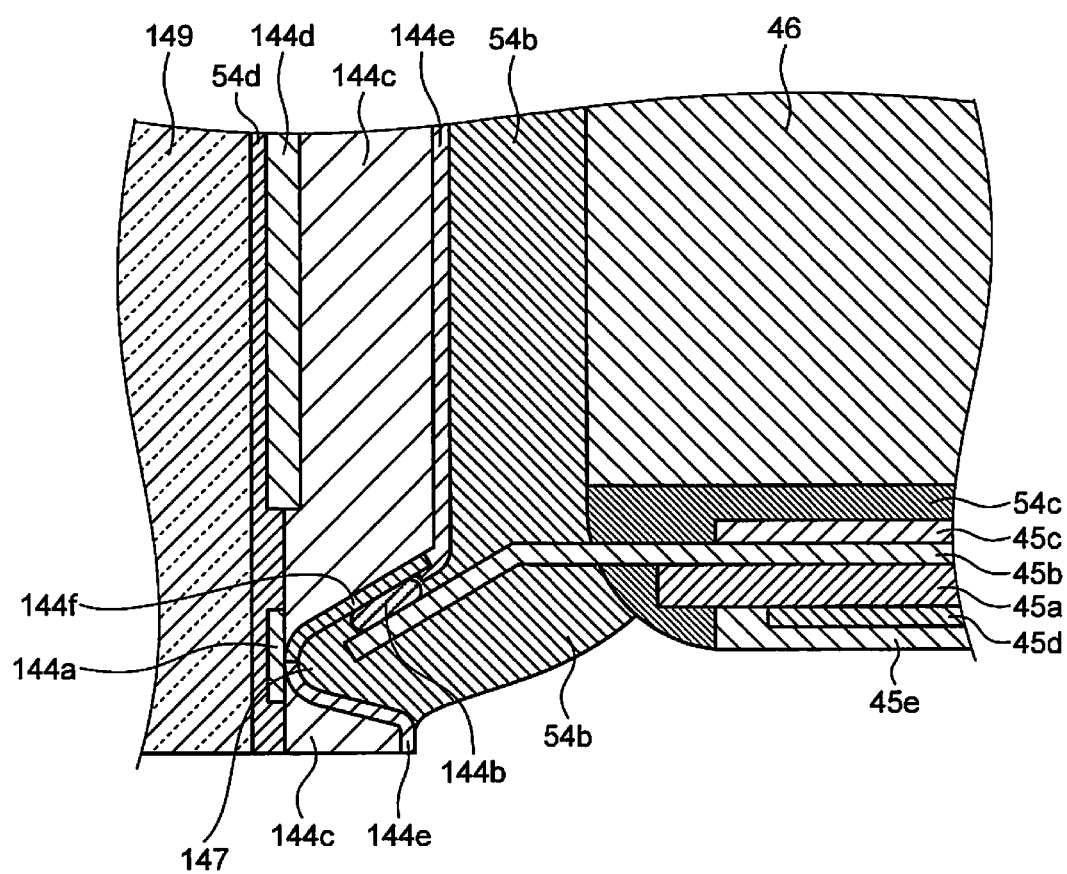
FIG. 21 is a cross-sectional view of a part of an imaging unit according to a modification of the second embodiment.

While the second embodiment is adapted such that the notch 145 is formed in the solid state image sensor 144 to expose the electrode pad 144a to the side of the FPC board 45 and that the oblique electrode 144f in conduction with the electrode pad 144a is formed on the notch 145, a groove-like opening instead of the notch 145 may be formed to then form the oblique electrode 144f in conduction with the electrode pad 144a in the opening. FIG. 21 is a cross-sectional view of a part of an imaging unit according to a modification of the second embodiment.

In a modification of the second embodiment, a groove-like opening 147 is formed in a solid state image sensor 144 to expose an electrode pad 144a on the side of an FPC board 45, and an oblique electrode 144f is formed in the opening 147 to electrically connect with the electrode pad 144a. Similar to the notch 145, the opening 147 is formed to traverse the surface of the solid state image sensor 144 on the side of the FPC board 45 such that a plurality of electrode pads 144a is all exposed on the side of the FPC board 45.

Since the opening 147 is a groove, an adhesive 54b for sealing the connection between an inner lead 45f and the oblique electrode 144f is contained in the opening 147 with no possibility of leaking outside the solid state image sensor 144, whereby an increase in size of the imaging unit can be prevented.

According to some embodiments, the inner lead is connected to the electrode pad by arranging the base material of the flexible printed circuit board on the outer side, whereby the imaging unit and the endoscope apparatus can be smaller in size.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An imaging unit comprising:
   a solid state image sensor having an electrode pad and a light-receiving surface and configured to receive light from a longitudinal direction and to perform photoelectric conversion on the received light to generate an electrical signal;
   a flexible printed circuit board having an inner lead connected to the electrode pad of the solid state image sensor, a length of the flexible printed circuit board extending in the longitudinal direction from the solid state image sensor in a direction opposite to where the light-receiving surface of the solid state image sensor is provided; and
   one or more electronic components mounted on a first surface of the flexible printed circuit board, the first surface being on a side where the solid state image sensor is provided, wherein
   the flexible printed circuit board includes a plurality of materials, each layered in a direction perpendicular to the longitudinal direction and in a plane parallel to the first surface, the plurality of materials comprising:
   an insulating base material;
   a first surface-side wiring layer on the base material on a side of the first surface;
   a first surface-side electrical insulating film for insulating the first surface-side wiring layer;
   a second surface-side wiring layer on the base material on a side of a second surface opposite to the first surface; and
   a second surface-side electrical insulating film for insulating the second surface-side wiring layer, and
   wherein the inner lead extends from the first surface-side wiring layer; and
   the one or more electronic components are mounted on the first surface of the flexible printed circuit board in the direction perpendicular to the longitudinal direction.

2. The imaging unit according to claim 1, wherein
   the solid state image sensor has a rectangular parallelepiped shape, and
   the inner lead is bent from a side of the solid state image sensor along the light-receiving surface.

3. The imaging unit according to claim 1, wherein
   the solid state image sensor includes a notch or an opening for exposing the electrode pad on a side of the flexible printed circuit board, and an oblique electrode to be connected to the electrode pad through the notch or the opening, and
   the inner lead is connected to the oblique electrode.

4. The imaging unit according to claim 3, wherein the inner lead is bent in such a way that the flexible printed circuit board is parallel to an optical axis direction of the solid state image sensor.

5. The imaging unit according to claim 3, wherein the flexible printed circuit board and the one or more electronic components are housed within a projected area on a surface orthogonal to an optical axis direction of the solid state image sensor.

6. The imaging unit according to claim 1, wherein a recognition mark for an alignment is formed on the first surface-side wiring layer to perform the alignment for mounting the solid state image sensor and for mounting the one or more electronic components.

7. An endoscope apparatus comprising an insertion unit, at a distal end of which the imaging unit according to claim 1 is provided.

8. The imaging unit according to claim 3, wherein the solid state image sensor further includes an examination pad formed on a back side of the solid state image sensor, the back side being opposite to a side of the light-receiving surface.

* * * * *